Figure 1:
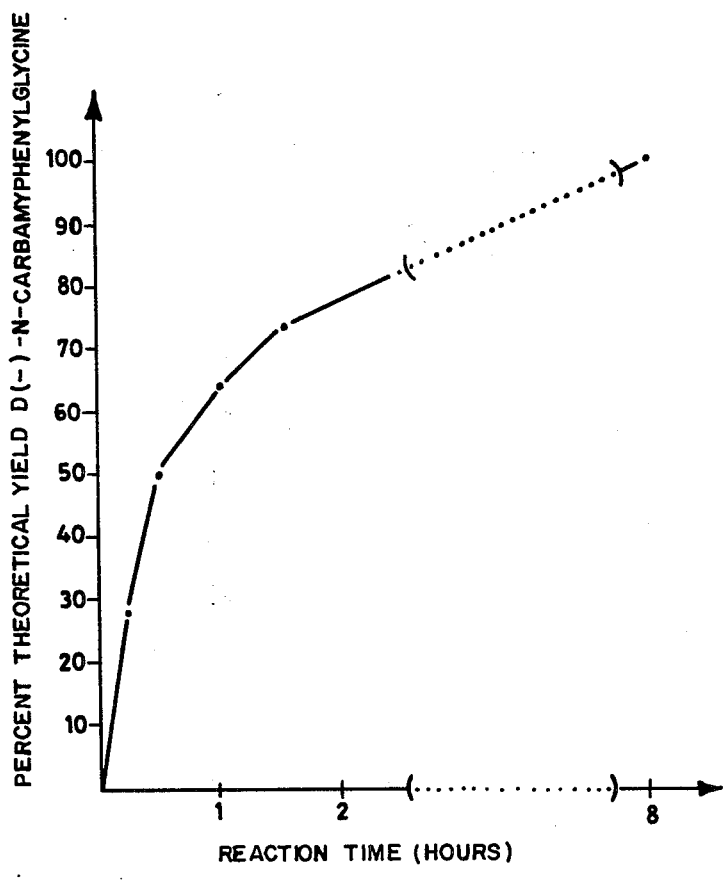

United States Patent [19]

Degen et al.

[11] 4,111,749
[45] Sep. 5, 1978

[54] METHOD OF CONVERTING RACEMIC HYDANTOINS INTO OPTICALLY ACTIVE AMINOACIDS

[75] Inventors: Ludwig Degen, Rome; Aurelio Viglia, Monterotondo (Rome); Eugenio Fascetti; Elena Perricone, both of Rome, all of Italy

[73] Assignee: Snamprogetti, S.p.A., Milan, Italy

[21] Appl. No.: 703,966

[22] Filed: Jul. 9, 1976

[30] Foreign Application Priority Data

Jul. 10, 1975 [IT] Italy ................................ 25252/75

[51] Int. Cl.$^2$ .............................................. C12D 13/06
[52] U.S. Cl. ........................................... 195/2; 195/29
[58] Field of Search .......................... 195/29, 62, 63, 2

[56] References Cited

U.S. PATENT DOCUMENTS 3,964,970  6/1976  Dinelli et al. ................ 195/29 X

FOREIGN PATENT DOCUMENTS 8,633  3/1970  Japan ................................ 195/29

OTHER PUBLICATIONS

Chemical Abstracts, vol. 73, 65026q; 1970.

Primary Examiner—Alvin E. Tanenholtz
Assistant Examiner—Robert J. Warden
Attorney, Agent, or Firm—Ralph M. Watson

[57] ABSTRACT

A method is disclosed for converting racemic hydantoins into optically active aminoacids, wherein microorganisms of the Pseudomonas genus are used to hydrolyze the hydantoins into derivatives of D,L-aminoacids.

Comparatively high temperatures and a definitely basic pH are favorable factors.

4 Claims, 1 Drawing Figure

METHOD OF CONVERTING RACEMIC HYDANTOINS INTO OPTICALLY ACTIVE AMINOACIDS

This invention relates to enzymatic complexes which are capable of converting racemic hydantoins into optically active aminoacids, and more particularly it relates to the hydrolysis of hydantoins into aminoacid derivatives having the "D" configuration, said hydrolysis resorting to the use of particular microorganisms which use hydantoin as a nitrogen source.

A few aminoacids, especially phenyl-glycine and p-hydroxyphenylglycine are important intermediates for the preparation of compounds which are widely used in the pharmaceutical industry.

A number of attempts have been made in the past to obtain D-aminoacids, but none of such methods could be carried out on an industrial scale.

The chemical methods as used hitherto for the separation of optical isomers are very expensive and give low yields. They are based on the use of camphorsulphonic acid.

Another method provides for a selective hydrolysis of the D-acyl-aminoacid with the acylase enzyme. However, the D-acylases are comparatively rare and always impure because of the presence of L-acylase, which makes the procedure difficult and is conducive to the obtainment of a product having poor optical purity.

The enzymatic hydrolysis which is the subject-matter of the present invention, conversely, permits the preparation of a single stereo-isomeric form of an aminoacid, or a derivative thereof, from a racemic compound.

A method for the enzymatic resolution of D,L-aminoacids or of their derivatives has already been suggested in U.S. Pat. No. 3,964,970. This method essentially comprises the step of subjecting to an enzymatic hydrolysis by hydropyrimidine hydrolase (E.C.3.5.2.2); extracted from calf's liver, the racemic form of compounds having the following general formula:

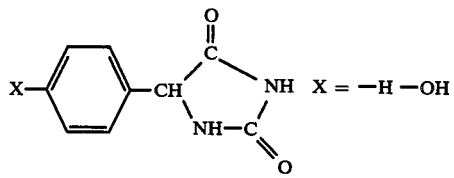

The hydrolysis takes place according to the pattern:

the Pseudomonas genus, which have never been employed in such a kind of reaction.

The method, the subject of the present invention, comprises the steps of producing the specific enzyme which is formed during the growth of microorganisms of the Pseudomonas class and hydrolyzing hydantoins into derivatives of D,L-aminoacids with this enzyme, wherein the enzyme can be used directly as a bacterial suspension or culture medium, or it can be extracted from the cells and the culture medium.

The test for the selective hydrolysis of hydantoin derivatives of D,L-aminoacids through microorganisms was carried out as follows: the bacterial strains, isolated from earth, plants, debris of various kinds, etc., as well as strains from bacterial collections were inoculated from slant into 250-mls flasks containing 50 mls of the following culture medium:

| Meat peptone | 10 grams per liter |
| Yeast extract | 10 grams per liter |
| Glucose | 5 grams per liter |
| NaCl | 3 grams per liter |
| 5-(D,L)-methylhydantoin | 1 gram per liter |
| pH = 7.2 | |

Sterilization 30 mins. at 110° C.

After 20 to 24 hours of incubation (orbital stirring) at 30° C., 500-ml flasks, containing 100 mls of the same medium, were incubated with 5 mls of the above pre-culture.

After 18 to 22 hours of additional incubation, the enzymatic reaction with the resting cells was carried out: in test tubes with 10 mls of phosphate buffer, 0.07 M, pH = 8.5, with 20 micromol/ml of 5-(D,L)-phenyl-hydantoin, there was added 1 ml of the bacterial suspensions (dry weight about 50 milligrams per ml). After 30 minutes of incubation at 30° C., the reaction with p-dimethylaminobenzaldehyde was carried out for the quantitative determination of the as-formed carbamyl derivative (J. Biol. Chem., 238, 3325 (1963). The strains which have been employed are tabulated in Table 1. Those of them which are identified by the numbers 942 and 945 have been deposited with the Centralbureau voor Schimmelcultures where they have been assigned the symbols CBS 145.75 and 146.75, respectively.

TABLE 1

| Strain | | N-carbamylphenylglycine as a % of the theoretical yield |
|---|---|---|
| Pseudomonas sp. | 940 | 41 |
| | 941 | 50 |
| | 942 | 64 |
| | 943 | 50 |

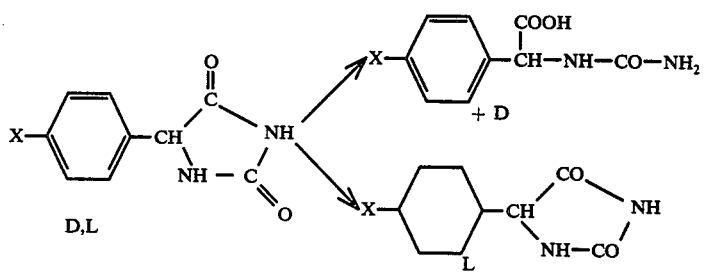

It has now been found that the enzymatic resolution of racemic compounds having the general formula (1) according to the pattern (2) can be carried out also with hydrolases which are supplied by microorganisms of

| | 944 | 50 |
| | 945 | 57 |
| | 946 | 50 |
| | 947 | 15 |
| | 948 | 15 |
| | 949 | 20 |

TABLE 1-continued

| Strain | | N-carbamylphenylglycine as a % of the theoretical yield |
|---|---|---|
| | 950 | 20 |
| | 951 | 20 |
| | 952 | 20 |
| | 953 | 20 |
| | 954 | 20 |
| | 955 | 20 |
| Pseudomonas fluorescens | 956 | 10 |
| Pseudomonas sp. | 957 | 41 |
| Pseudomonas ATCC | 11299 | 9 |
| Pseudomonas oleovorans CL | 59 | 17 |
| Pseudomonas desmolyticum NCIB | 8859 | 25 |
| Pseudomonas fluoroscens ATCC | 11250 | 25 |
| Pseudomonas putida ATCC | 12633 | 14 |

The bacterial strains listed in TABLE 1 grow well in all the common laboratory media. They are all capable of using hydantoin as a single nitrogen source. The growth takes place at a temperature ranging from 5° C. to 40° C., the optimum being between 25° C. and 30° C.

As regards the classification by genera, the scheme of the Bergey's Manual, 7th Edition was followed together with the recommendations by Lysenko (J. Gen. Microbiol. 25, 379 (1961) and by Stanier, Palleroni, Doudoroff (J. Gen. Microbiol. 43, 159–271 (1966).

It has been found that during the enzymatic hydrolysis of D-hydantoin at an alkaline pH (pH 7–10) a nonenzymatic racemization of the remaining L-hydantoin takes place. For this reason, and as a result of the continuous removal of D-hydantoin by enzymatic hydrolysis, all the carbamyl derivative obtained at the end of the reaction is of the D-form.

The identity of D(−)-N-carbamylphenylglycine was evidenced after crystallization of the reaction product, on the basis of the IR, NMR, and mass spectra and the elemental analysis.

The specific rotation is $[\alpha]_D^{25} = -137°$ ($c = 1\%$ in 1N $NH_4OH$) corresponding to the one as reported in the literature.

The racemization rate of L-hydantoin is a function of the temperature and of the pH and is the faster, the higher is the temperature and the more basic is the pH. However, by working at a pH in the vicinity of 7.5, the racemization rate is sufficiently high so as not to limit the reaction speed.

The temperature of the enzymatic reaction can be maintained between 10° C. and 60° C. For practical reasons, however, temperatures comprised between 25° C. and 40° C. are preferred.

According to the present invention, the hydrolysis of the hydantoins takes place not only in the presence of microorganisms which are being grown or in the presence of intact cells of them, but also in extracts of the above enumerated microorganisms. The microorganisms can be cultured, for example, in a liquid nutrient medium so as to obtain an accumulation of hydrolase in the cells and the DL-hydantoins can be added subsequently to the culture. The enzymatic reaction can also be carried out with the so-called resting cells. In this case the bacterial cells are recovered from the culture medium, washed and suspended in an appropriate buffered medium to which the racemic hydantoin is added.

In addition, it is possible to use preparations which contain the hydrolases, such as extracts or concentrates of them, raw or purified hydrolase preparations which have been obtained from cells of the above enumerated microorganisms. Lastly, raw or purified hydrolases can be used, which have been immobilized through combinations with macromolecular compounds.

Other procedures will become apparent from the ensuing examples which are given only for the purpose of illustrating the present invention.

EXAMPLE 1

To 100 mls of a broth culture in the above reported medium of the strain Pseudomonas sp. 942 in a 500-ml flask there were added at the 24th hour of incubation (orbital stirring) at 30° C., 100 mls of a phosphate buffer (0.14 M) pH = 8.5, which contained 30 micromol/ml or 5-(D,L)-phenyl-hydantoin.

After 5 additional hours of incubation, under the same conditions, the as-formed N-carbamylphenylglycine was determined.

From 530 milligrams of 5-(D,L)-phenylhydantoin, there were formed 525 milligrams of N-carbamylphenylglycine, which correspond to a yield of about 90%.

EXAMPLE 2

A culture broth was prepared, having the above reported composition and which contained 1 gram per liter of 5-(D,L)-methylhydantoin.

The pH was adjusted to 7.2 with soda and the medium was distributed into 50-ml portions in 250-ml flasks. Upon sterilization at 110° C. during 30 mins., the flasks were inoculated with a culture of Pseudomonas sp. 942 from a slant which contained the same medium with the 2% of agar (DIFCO) and incubated at 30° C. during 20 hours with orbital stirring (220 rpm).

With this pre-culture (Optical Density, at 550 nm: 0.400; dilution 1:10) there were inoculated 5 mls in 500-ml flasks which contained 100 mls of the same medium and the culture was incubated at 30° C. with orbital stirring (220 rpm) during 18 hours (last phase of the exponential growth). The cells were then collected by centrifugation (5,000 g, 20 mins) and washed three times in a buffered physiological salt solution and finally suspended in a phosphate salt buffer pH = 8.5, 0.07 M: resting cells.

For the enzymatic hydrolysis there were incubated at 30° C. with orbital stirring (220 rpm) in 250-ml flasks, 64 mls of the reaction mixture composed of: 260 milligrams of bacteria (dry weight) and 20 micromols/ml of D,L-phenylhydantoin (= 3.52 milligrams/ml). At various time intervals, the product of the hydrolysis, i.e. D-carbamylphenylglycine, was determined with a colorimetric method (J. Biol. Chem. 238, 3325 (1963) at 438 nm. FIG. 1 shows the results, in terms of percent of the theoretical yield of the as-formed carbamylderivative: on the abscissae there are reported the times (hours) and on the ordinates the percentages of D(−)-N-carbamylphenylglycine which had been formed.

EXAMPLE 3

There was prepared a semisynthetic medium having the following composition:

| | |
|---|---|
| $Na_2HPO_4$ | 7.05 grams per liter |
| $KH_2PO_4$ | 2.72 grams per liter |
| $(NH_4)_2SO_4$ | 5.0 grams per liter |

| -continued | | |
|---|---|---|
| MgSO$_4$ | 0.2 | grams per liter |
| MnSO$_4$ | 0.45 | milligrams per liter |
| FeSO$_4$ . 7H$_2$O | 5.5 | milligrams per liter |
| Glucose | 10 | grams per liter |
| Yeast Extract | 0.2 | grams per liter |
| 5-(D,L)-methylhydantoin | 1.0 | grams per liter |

The medium was distributed in 50-ml portions in 250-ml flasks, and in 100-ml portions in 500-ml flasks and sterilized during 30 mins. at 110° C.

For the pre-culture, the 250-ml flasks were inoculated from slant with a culture of the Pseudomonas sp. 942 strain and incubated as in Example 2 during 24 hours at 30° C.

From this culture (Optical Density at 550 nm : 0.245; dilution 1 : 10) there were inoculated 5 mls in 500-ml flasks. After a 19-hour incubation at 30° C., as above, the resting cells were prepared as in Example 2.

Enzymatic hydrolysis was carried out at 30° C. in a reaction mixture which contained in 64 mls of buffer, 280 milligrams of bacteria (on dry weight basis) and 20 micromols/ml of 5-(D,L)-phenylhydantoin. After 5, 10 and 15 minutes, the quantity of the as-formed carbamyl derivative was determined.

TABLE 2

| Time minutes | 5 | 10 | 15 |
|---|---|---|---|
| micromol/ml of the formed carbamyl derivative | 1.15 | 2.05 | 3.00 |

EXAMPLE 4

Bacterial cells were prepared of the strain Pseudomonas sp. 942 as described in Example 2. A suspension of them (42 milligrams per milliter of dry cells) in a phosphate salt buffer, 0.1 M, pH = 8, was subjected to mechanical break by using a "Manto-Gaulin" homogenizer working at the pressure of 850 kg/sq. cm at a temperature below 24° C.

The cellular debris was separated from the extract by centrifugation (25,000 g, 30 mins.).

To 950 mls of phosphate salt buffer, pH = 7.7, containing 2.12 grams of 5-(D,L)-phenylhydantoin there were added 50 mls of the extract which contained 8,500 U of the enzyme. (1U is the amount of enzyme which converts in a phosphate buffer, pH = 7.7 at 30° C., containing 12 micromol/ml of 5-(D,L)-phenylhydantoin, 1 micromol/ml of the substrate, in 60 minutes).

After 1 hour at 30° C. there had been formed 1.7 grams of D-carbamylderivative corresponding to about 80% of the total hydrolysis.

EXAMPLE 5

As in Example 4, there were added to 993 mls of substrate, 7 mls of a preparation of the extract which had been purified about 7 times. After 1 hour at 30° C. there had been formed 1.7 grams of D-carbamyl derivative corresponding to about 80% of the total hydrolysis.

EXAMPLE 6

Under the same conditions as in Example 2, there were obtained, after 30 minutes at 30° C., with the strain Pseudomonas sp. 945, from 352 milligrams of 5-(D,L)-phenylhydantoin, 220 milligrams of N-carbamylphenylglycine, which correspond to about 57% of the theoretical yield.

What we claim is:

1. The method of preparing the "D" form of an optically active aminoacid derivative from a racemic hydantoin which comprises, subjecting said racemic hydantoin to hydrolysis in the presence of an enzymatic complex derived from the strain of microorganisms of the genus Pseudomona which is designated sp. 942 (CBS 145.75) or sp. 945 (CBS 146.75), said hydrolysis being effected at a temperature in the range of from 10° to 60° C., and at an alkaline pH in the range of from pH 7 to pH 10.

2. The method of preparing the "D" form of an optically active aminoacid derivative represented by the general formula:

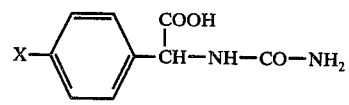

wherein X is H or OH, which comprises contacting a racemic hydantoin represented by the formula:

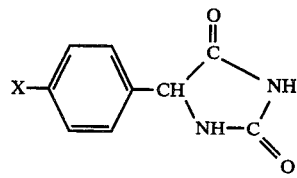

wherein X has the significance given above, with an enzymatic complex derived from the strain of microorganisms of the genus Pseudomona which is designated sp. 942 (CBS 145.75) or sp. 945 (CBS 146.75), at a temperature in the range of from 10° to 60° C., and at an alkaline pH in the range of from pH 7 to pH 10, so that the "D" form of said hydantoin is hydrolyzed to said aminoacid derivative and any remaining "L" form of said hydantoin undergoes racemization.

3. The method of preparing D(-)-N-carbamylphenylglycine from 5-(D,L)-phenylhydantoin which comprises, contacting said hydantoin with an enzymatic complex derived from the strain of microorganisms of the genus Pseudomonas which is designated sp. 942 (CBS 145.75), at a temperature in the range of from 25° to 40° C., and at an alkaline pH.

4. The method of preparing D(-)-N-carbamylphenylglycine from 5(D,L)-phenylhydantoin which comprises, contacting said hydantoin with an enzymatic complex derived from the strain of microorganisms of the genus Pseudomonas which is designated sp. 945 (CBS 146.75), at a temperature in the range of from 25° to 40° C., and at an alkaline pH.

* * * * *